(12) United States Patent
Kassman

(10) Patent No.: US 6,918,392 B2
(45) Date of Patent: Jul. 19, 2005

(54) CONDOM APPLICATOR (76) Inventor: Leon B. Kassman, 245 E. 24th St., New York, NY (US) 10010

( * ) Notice: Subject to any disclaimer, the term of this patent is extended or adjusted under 35 U.S.C. 154(b) by 496 days.

(21) Appl. No.: 10/016,219

(22) Filed: Dec. 6, 2001

(65) Prior Publication Data
US 2002/0069881 A1 Jun. 13, 2002

Related U.S. Application Data (60) Provisional application No. 60/251,827, filed on Dec. 7, 2000.

(51) Int. Cl.⁷ .................................................. A61F 6/04
(52) U.S. Cl. ...................... 128/844; 128/842; 128/918; 604/349; 206/69; 427/2.3
(58) Field of Search ................................ 128/844, 842, 128/918, 917, 898, 879, 880; 604/347, 348, 349, 350, 351, 352, 353; 206/69; 427/2.1, 2.3

(56) References Cited

U.S. PATENT DOCUMENTS

| 4,961,734 | A | * | 10/1990 | Kassman | ...................... 604/349 |
| 5,205,298 | A | * | 4/1993 | Hurst | .......................... 128/844 |
| 5,549,196 | A | * | 8/1996 | Kassman | ...................... 206/69 |
| 5,885,205 | A | * | 3/1999 | Kassman | .................... 128/842 |
| 6,569,083 | B1 | * | 5/2003 | Kassman | .................... 128/844 |

* cited by examiner

Primary Examiner—Fadi H. Dahbour
(74) Attorney, Agent, or Firm—Abelman, Frayne & Schwab (57) ABSTRACT A condom applicator supports a condom in a substantially unstretched condition until just before use, and then expands the cross-section of the condom.

29 Claims, 10 Drawing Sheets

CONDOM APPLICATOR

This application claims benefit of Provisional application 60/251,827 filed Dec. 7, 2000.

FIELD OF THE INVENTION

This invention relates to an applicator for assisting the donning of a condom.

BACKGROUND OF THE INVENTION

The utilization of condoms (regardless of whether composed of natural latex, elastomeric polymer, natural animal intestine, or any other natural or manmade material) for contraception and for protection against sexually transmitted diseases has increased. Nevertheless, the frequency of use of condoms has been limited by certain properties intrinsic to their packaging and orientation during use.

For example, users report that condoms, particularly condoms packaged with silicone as a lubricant, often leave a residue on the hands after the condoms are touched. As another example, in many cases the condoms are applied in the wrong direction, since traditional packaging furnishes little or no instruction or other visible markings or evidence regarding the orientation for applying the condom.

A further problem, discussed in more detail below, is that when a condom is packaged in a manner such that it is pre-stretched, especially when it is pre-stretched to a substantial degree, the material of the condom may suffer fatigue stress over time, rendering the condom unusable or ineffective.

These and other properties of prior art condoms and condom applicators have dissuaded and/or prevented those men who have experienced difficulty in condom application from consistently using condoms.

Various devices have been suggested or made to enable men to correctly orient and apply condoms or to provide for more sterile application of condoms or both. Examples of such devices are disclosed in U.S. Pat. No. 5,662,214 to Wood, U.S. Pat. No. 5,478,193 to Vonier et al., U.S. Pat. No. 5,549,120 to Persson et al., U.S. Pat. Nos. 4,993,431 and 4,993,433 to Reddy, U.S. Pat. No. 5,170,887 to Potts et al., U.S. Pat. No. 5,205,298 to Hurst, U.S. Pat. No. 4,972,850 to Broad, U.S. Pat. No. 5,437,286 to Stratton, U.S. Pat. No. 5,666,971 to Anatolievich, U.S. Pat. No. 5,638,949 to Jones, U.S. Pat. No. 5,666,972 to Gifford, U.S. Pat. No. 5,551,612 to Hochfeld, U.S. Pat. No. 5,651,374 to Wester and U.S. Pat. No. 5,549,196 to Kassman.

Conventionally, condoms are manufactured and shipped in a number of forms including fully rolled, partially unrolled and fully unrolled. When a condom is fully rolled, only its closed end (which may or may not include its reservoir tip) is not rolled. For both a fully rolled condom and a partially rolled condom, the inter-rolling of its wall forms a circular bead. The thickness of the bead varies from condom to condom, depending on the thickness of the material composing the condom, the compaction of the roll and the length of the portion of the condom that is rolled. The rolled condom, which normally forms a circle with its circumference, has an inner diameter measured across the flat unrolled portion of the condom and an outer diameter measured across the entire rolled form and including the width of the inter-rolled walls or bead.

None of the previously mentioned patents provide a means of both holding the condom initially during storage in an unstretched or nearly unstretched (moderately stretched) state and then during use allowing sufficient force to be exerted on the condom to expand its diameter to a size permitting it to fit easily over an erect penis. Two of the references cited, Kassman and Wood, each provide a respective means of shipping condoms wherein the condoms are already pre-stretched to one degree or another on a form. Both references disclose a container closed at one end and open at the other end at which a condom is to be applied. The construction of Kassman's device permits a partial vacuum to be created when a cylinder, having a wall containing bellows to which a condom has been pre-applied, is pulled open or opens of its own accord, thus expanding the condom. The condom, which would normally be applied to Kassman's applicator at the factory, is pre-stretched, in either its rolled or unrolled diameter, to an extent of at least 50% of its manufactured diameter.

Similarly, Wood provides for a bell-shaped body when, while not exerting any vacuum force, manages to expand the condom by virtue of transferring the force exerted on the outside of the body when pressing it open and thus deforming its side walls, the side walls carrying with them the attached condom. To achieve this, the attached condom in Wood is pre-stretched to an amount in excess of approximately 75% of its originally manufactured unstretched diameter.

Both the Kassman and Wood structures require a condom to be normally pre-stretched prior to its intended use for a time which may be, if the packaged condom is stored, for up to five years. This results in fatigue stress to the packaged condom, in addition to those stresses normally experienced by the condom upon exposure to air, other gases or normal wear and tear occurring to traditionally packaged conventional condoms. As noted above, these stresses may lead to condom failure.

Accordingly, there has been a long-felt need to provide a condom applicator that both effectively packages the condom for long-term storage without deterioration and enables easy and efficient application of the condom.

SUMMARY OF THE INVENTION

It is therefore an object of the present invention to provide a condom applicator that avoids the above-described difficulties of the prior art.

It is a further object of the present invention to provide a condom applicator that holds a condom in an unstretched or substantially unstretched condition to avoid stress fatigue.

It is still a further object of the present invention to provide a condom applicator that can be easily expanded to expand the condom correspondingly for application.

It is another object of the present invention to provide a condom applicator that reduces the amount of handling required during application to reduce the amount of silicone or other lubricant transferred to the user's hands.

It is still another object of the present invention to provide a condom applicator that in any event permits full insertion of the penis into the stretched condom.

In particular, the present invention effects substantial improvement over the prior art by permitting and enabling the following:

1) the rapid application of any condom using only one hand;

2) packaging which aids in the correct orientation of the condom prior to donning;

3) allowing stretching of the condom immediately before use in order to ease the application procedure;

4) a means of packaging a condom without stretching it until immediately before use;

5) a means of limiting contact of the condom with the hands during application;

6) a means of packaging condoms:

7) a means of expanding a condom applicator;

8) a means of protecting condoms more securely during shipment; and 9) a means of correctly orienting condoms within their packaging.

The above and other objects are achieved by the present invention which, in one embodiment, is directed to a condom applicator for supporting a condom, the condom in a substantially unstretched condition having an inner diameter defining a condom circumference at an open cross-section thereof, and the applicator comprising an axial tubular wall having first and second axially opposed open ends and an outer surface. The wall has a compressed configuration in which the first open end defines a compressed opening having an applicator circumference not substantially greater than the condom circumference, and an expanded configuration in which the first open end defines an expanded opening greater than the applicator circumference and sized to permit axial insertion of a penis.

The applicator further comprises means for detachably securing the condom at the first open end such that the condom circumference conforms to the applicator circumference around the outer surface of the wall with the cross-section of the condom covering the first open end. As a result of this structure, the cross-section of the condom is expanded to the size of the expanded opening by expanding the wall from its compressed configuration with the condom secured thereto to its expanded configuration with the condom secured thereto.

In accordance with an advantageous aspect of the present invention, the expanded opening may be substantially elliptical.

The present invention significantly reduces the stresses caused by prior art devices due to pre-stretching by substantially or totally eliminating the need to stretch the condom until immediately, often less than five minutes, before use.

The present invention also provides a means of shipping condoms (made of any natural or manmade material) more securely, and a means of improving the application of condoms. To achieve these and other objects, each condom may be attached to and nested in a flexible form (composed of, for example, any polymer, metal, reinforced paper or impregnated cardboard). The condom is pre-stretched to an insubstantial, or at most moderate, degree prior to shipping, and the condom can remain in this state until immediately prior to use.

In a preferred embodiment, the device includes means for assisting expansion of the applicator wall from its compressed configuration with the condom secured thereto to its expanded configuration with the condom secured thereto. The expansion assistance means may include at least one gripping section on the outer surface of the wall, the gripping section having a frictional surface suitable for engaging skin, whereby the applicator may be held by hand at the gripping section while being expanded from its compressed configuration to its expanded configuration.

Alternatively or in combination with such gripping sections, the expansion assistance means may include one or more pull tabs. Advantageously, when the wall in its compressed configuration is folded to have an interior fold line at which the outer surface of two portions of the wall are in contact, the expansion assistance means may further include a pull tab attached substantially at the interior fold line at a position opposed to the gripping sections and extending beyond the applicator circumference, so that the applicator may be held by hand at the gripping section while being expanded from its compressed configuration to its expanded configuration by tension on the pull tab.

These and other objects, features and advantages of the present invention will be apparent from the following detailed description of the preferred embodiments taken in conjunction with the following drawings, wherein like reference numerals denote like elements.

DETAILED DESCRIPTION OF THE PREFERRED EMBODIMENTS

Figures 1, 2, 5:
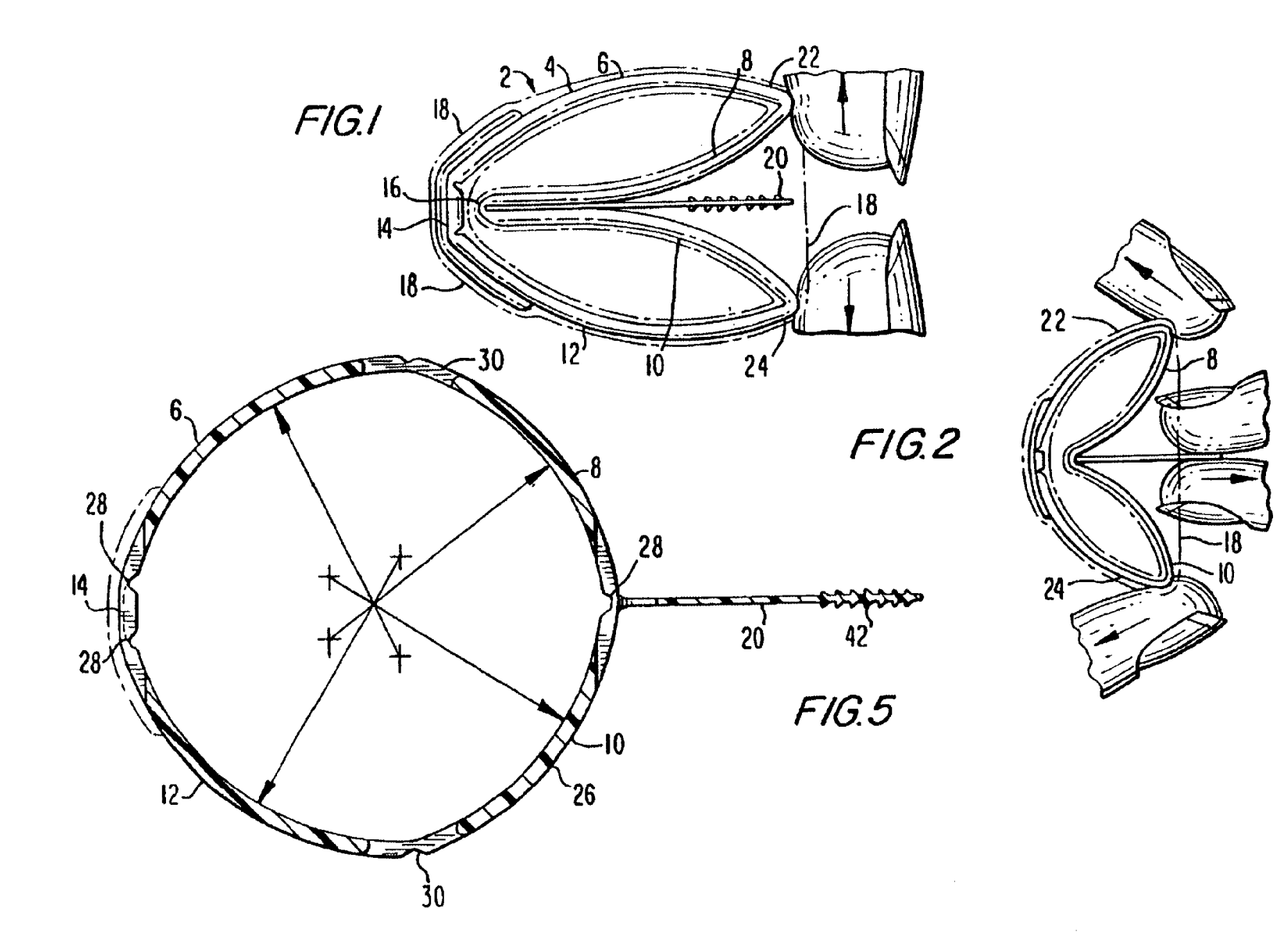
FIG. 1 is a top view of a condom applicator in accordance with a first preferred embodiment of the present invention, with the condom applicator about to be opened from its compressed configuration.
FIG. 2 is a top view of the condom applicator of FIG. 1 in the process of being opened to its expanded configuration.
FIG. 5 is a top view of the condom applicator of FIG. 2 after having been opened to its expanded configuration.

With reference to FIG. 1, a condom applicator 2 in accordance with a first embodiment of the present invention is illustrated in its compressed configuration in which it is stored until just prior to use. The applicator 2 is generally in the form of a tube, viewed axially from the top in FIG. 1, that may be folded or otherwise compressed to reduce the size of its cross-section.

More particularly, in the embodiment of FIG. 1, the applicator 2 is formed of an axial tubular wall 4 having four axial wall sections 6, 8, 10 and 12 and a hinge section 14. In the compressed configuration, the wall 4 is folded to have an interior fold line 16 between the wall sections 8 and 10 at which the outer surface of these two portions of the wall 4 are in contact. Each wall section has an outward convex shape, so that when the wall 4 is expanded it will form an expanded opening that is substantially elliptical.

FIG. 1 illustrates in a dashed line an important feature of the present invention: the applicator circumference 18. This applicator circumference 18 goes all the way around the outer surface of the wall 4 but is not the same as the perimeter of the wall 4, which follows the ins and outs of the wall 4 in its different configurations. Rather, the applicator circumference 18 is the distance around the outer extent of the wall 4 in a particular configuration, and may be viewed as the line that would be taken by, for example, a conventional rubber band slipped around the wall 4. As shown in FIG. 1, the applicator circumference 18 of the wall in its compressed configuration is less than the wall perimeter, since the applicator circumference does not extend inwardly toward the interior fold line 16.

Figures 3, 4:
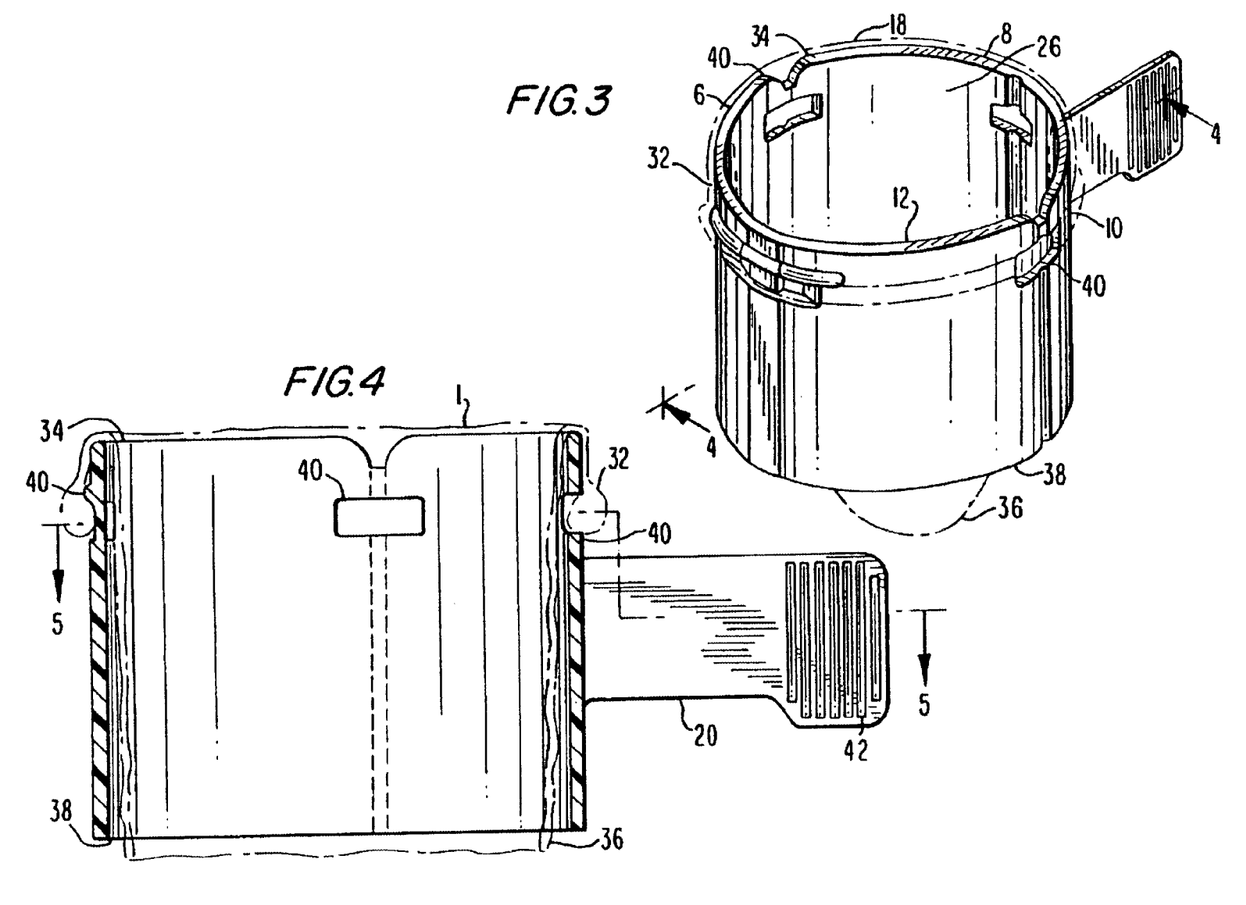
FIG. 3 is a perspective view of the condom applicator of FIG. 2 after having been opened to its expanded configuration.
FIG. 4 is a cross-sectional view of the condom applicator of FIG. 3 taken along the direction of the arrows.

In accordance with the present invention, the applicator circumference 18 is intended to be at its smallest when the wall 4 is in its compressed configuration as shown in FIG. 1. As shown in FIGS. 2 and 3, as the wall 4 is in the process of being opened (FIG. 2) and is fully opened to be in its extended configuration (FIG. 3), the applicator circumference 18 increases. Since a condom 1 is intended to be mounted on the wall 4, as described below, the circumference of the mounted condom 1 will conform to the applicator circumference 18 at the outer surface of the wall 4 and will be correspondingly expanded as the applicator circumference 18 is expanded. This in turn enables the condom 1 to be mounted in an unstretched or substantially unstretched condition and stored in that condition until just before its use, when expansion of the wall 4 will expand the cross-section of the condom 1 to have the size of the expanded opening of the wall 4.

Returning to FIG. 1, the applicator 2 advantageously includes expansion assistance means, which in this embodiment includes a pull tab 20 attached substantially at the interior fold line 16. In FIG. 1, the pull tab 20 is not showing as extending beyond the applicator circumference 18, so that it will not touch or interfere with the condom. However, it is possible for the pull tab 20 to extend beyond the applicator circumference 20 so that it may be more easily gripped for opening the applicator 2 by tension on the pull tab 20.

FIG. 1 shows how the applicator 2 may be opened by pushing apart the two wings 22, 24 of the applicator 2 on either side of the fold line 16. As the wings 22, 24 are pushed apart, the fold line 16 will start to move outwardly. FIG. 2 shows how tension on the pull tab 20 will assist this outward movement. When the wings 22, 24 have been pushed apart sufficiently, the wall 4 will pop open to have a substantially elliptical expanded opening 26, as shown in FIG. 3 and in cross-section in FIG. 5. The expanded opening 26 is sized to permit axial insertion of a penis.

As shown in FIG. 5, the wall 4 has inner axial grooves 28 and outer axial grooves 30 between adjacent ones of the wall sections 6–12 and the hinge section 14. This facilitates the bending of the wall 4 into the compressed configuration.

It is noted that the dashed line indicating the applicator circumference 18 may also be viewed as illustrating the condom 1 in phantom. Particularly in FIGS. 3 and 4, the bead 32 of the condom 1 is shown positioned and secured around the wall 4 at the top open end 34. The rest of the condom 1 extends over the wall 4 and into the interior of the applicator 2, with the tip 36 of the condom 1 extending somewhat out of the bottom open end 38. Depending on how much the condom 1 is rolled, the tip 36 may be within the interior of the applicator 2. It will be understood that the bead 32 of the condom 1 is positioned on the wall 4 when the wall 4 is in its compressed configuration as shown in FIG. 1, with the cross-section of the condom covering the top open end 34. Therefore, even if the tip 36 is inserted into the interior of the applicator 2, the condom cross-section may still be considered as covering the top open end 34.

As also shown in FIGS. 3 and 4, the wall 4 contains other structure for securing the bead 32 of the condom 1 to the applicator 2. Advantageously, this structure includes notches that extend partially or entirely through the wall 4 and into which the bead 32 fits. In this embodiment, the notches are in the form of windows 40 through the wall 4, advantageously positioned at the axial grooves 28, 30. When the bead 32 is fitted over the top open end 34 and at least partway into the windows 40, it is held securely enough to remain in place during shipment and storage, but may be readily removed as part of the application process.

As shown in FIGS. 4 and 5, the pull tab 20 is advantageously equipped with triangular ridges 42 to improve the grip of fingers. Although not illustrated in FIG. 4, one or more gripping sections may be created on the outer surface of the wall 4 at a position opposite that of the pull tab 20, with ridges or some other frictional surface. The applicator 2 may then be opened by holding it at the gripping sections and pulling on the pull tab 20.

In order to strengthen the hinge section 14, a backing strip 44 may be applied. As shown in FIG. 3, the backing strip 44 can be in the form of a ridge positioned just above one of the windows 40 so that it assists in securing the bead 32 on the wall 4.

Thus, the condom applicator 2 is prepared by first placing it in its compressed configuration and then fitting the bead 32 of the condom 1 over the top open end 34 and into the windows 40. The compressed configuration has a compressed opening that defines the applicator circumference 18 for this configuration. As noted above, the condom in its substantially unstretched configuration has an inner diameter of its bead 32 or unrolled rim defining a condom circumference at the open top cross-section thereof. The applicator circumference for the compressed configuration is not substantially greater than this condom circumference. Therefore, when the condom is fitted onto the wall 4 with the wall 4 in its compressed configuration, the condom itself will remain substantially unstretched.

If desired, the tip 36 of the condom 1 can be tucked into the interior of the applicator 2 for safekeeping during storage.

The applicator 2 is then packaged to be held in its compressed configuration, for example by a keeper band.

In order to use the condom, the keeper band or other packaging holding the applicator 2 in the compressed configuration is removed. Advantageously, the applicator 2 will not automatically spring into its expanded configuration upon the removal of the packaging, although this is possible in some embodiments of the present invention. In this embodiment, the applicator 2 may open to a small extent, but the condom will still not be substantially stretched. At his convenience, the user can open the applicator 2 to its expanded configuration by pushing apart the wings 22, 24 and/or pulling on the pull tab 20. In the expanded configuration, the applicator circumference, and hence the condom cross-section, expands to match the substantially elliptical expanded opening. The penis can then be axially inserted down through the top open end 34 and into the condom within the applicator 2. Because the bottom end 38 of the applicator 2 is also open, the penis can be inserted as far as desired. At this point, the condom will be fitting snugly around the penis, and the applicator 2 may be easily removed simple by pulling it downward.

Figure 6:
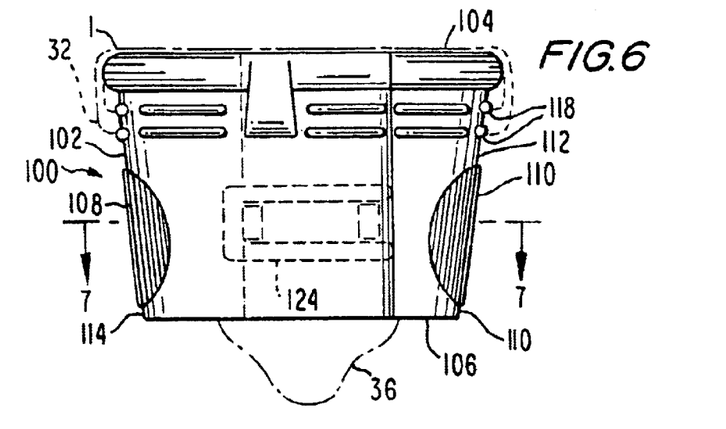
FIG. 6 is a side elevational view of a condom applicator in accordance with a second preferred embodiment of the present invention, in its compressed configuration and with an attached condom shown in phantom.

FIG. 6 illustrates another preferred embodiment of the condom applicator in accordance with the present invention. As shown therein, the applicator 100 includes an axial tubular wall 102 having a first, upper open end 104 and a second, lower open end 106. Two opposed gripping sections 108, 110 on the outer surface 112 of the wall 102 have a roughened, frictional surface suitable for engaging the skin of the user's hand.

Figure 7:
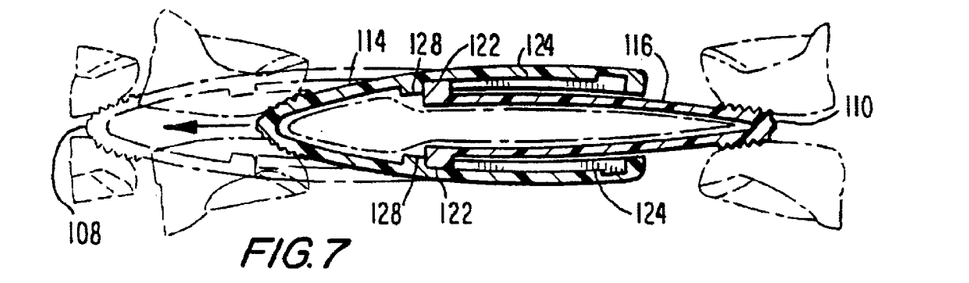
FIG. 7 is a top view of the condom applicator of FIG. 6 in the process of being opened to its expanded configuration.

The applicator 100 is constructed as a sectioned applicator form made of two separate folded halves 114, 116, fitted to lie within each other's contour. In FIGS. 6 and 7, the applicator 100 is shown in its compressed configuration, with halves 114, 116 lying flat and overlapping. Two rows of ridges 118 project outwardly from the outer surface 112, with each ridge and each row of ridges extending substantially parallel to the upper open end 104 at least partially around the wall 102. By having rows of ridges, rather than one or more single ridges extending entirely around the wall 102 along each half 114, 116, the two halves can be more flexible for moving the applicator 100 to its expanded configuration. However, it is also possible to construct the applicator 100 with one or more such single ridges.

The immobilization of the condom may be aided during shipping by a thin piece of particle filler attached to the inner surface of the wall 102, which is placed in juxtaposition to the condom 1.

As in the previous embodiment, the applicator 100 supports a condom 1 which has, in a substantially unstretched condition, an inner diameter defining a condom circumference at an open cross-section. The bead 32 of the condom 1 is secured to the applicator 100 by being fitted, at least partially, between the two rows of ridges 118, which are spaced apart by a distance designed to hold the bead 32 with the appropriate strength. In the compressed configuration shown in FIGS. 6 and 7, the upper open end 104 defines a compressed opening having an applicator circumference not substantially greater than the condom circumference, so that the bead 32 is not substantially stretched and applies little or no compressive force. The lower portion 36 of the condom is either extended flat over the upper open end 104 or is nested within the applicator 100.

Figure 8:
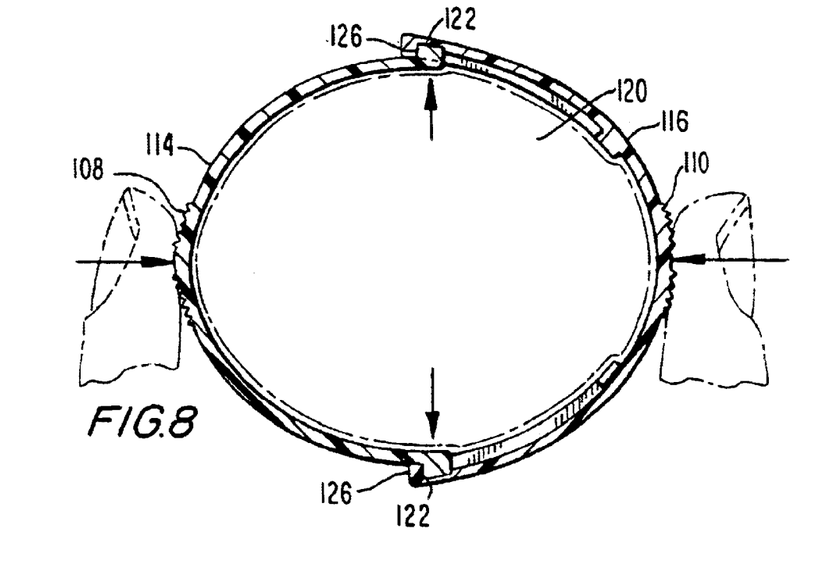
FIG. 8 is a top view of the condom applicator of FIG. 6 after having been opened to its expanded configuration.

As in the previous embodiment, the applicator 100 is made of any natural or man-made elastomeric material and is capable of assuming an expanded configuration, shown in FIG. 8, in which the upper open end 104 has an expanded opening 120 that is advantageously approximately circular or elliptical and sized to permit axial insertion of a penis.

The two halves 114, 116 are fitted together to be slidable with respect to each other without disconnection. In this embodiment, one or both of the halves has protrusions 122 on the outer surface that ride in complementary internal tracks 124 on the inner surface of the other half. The internal tracks 124 are shown in dotted lines in FIG. 6, since they are hidden from view. The protrusions 122 cooperate with the internal tracks 124 to guide the halves 114, 116 in achieving compatible outward and inward trajectories each time a force is applied to pull open or return each of the halves 114, 116 from or to the compressed, interleaved configuration shown in FIG. 6. The internal tracks 124 have internal stops or snaps 126 preventing the protrusions 120 from being pulled entirely out of the tracks 122, and thereby pulling the halves 114, 116 fully apart. The halves 114, 116 also include internal stops 128 to prevent the two halves from being pushed together too far.

The internal stops 126 also serve, when the halves 114, 116 have been pulled apart to achieve their fullest permitted extension, to cause the halves 114, 116 to snap into a locked position. This locked position prevents the halves 114, 116 from returning to their former interleaved position despite compressive pressure being exerted on the halves 114, 116.

The pulling apart of the halves 114, 116 is achieved by a user pulling on the two halves 114, 116 as shown in FIG. 7 in the direction of the arrow with sufficient force to stretch the condom 1 until the halves snap into their fully open position. The necessary pulling action may be eased by using the gripping portions 108, 110, which provide sufficient friction to allow the halves to be pulled apart and locked into position. Then, as shown in FIG. 8, the user pushes on opposite sides of the applicator 100, for example at the gripping portions 108, 110, to open the applicator 110 to present the substantially elliptical expanded opening 120.

Figures 9, 10:
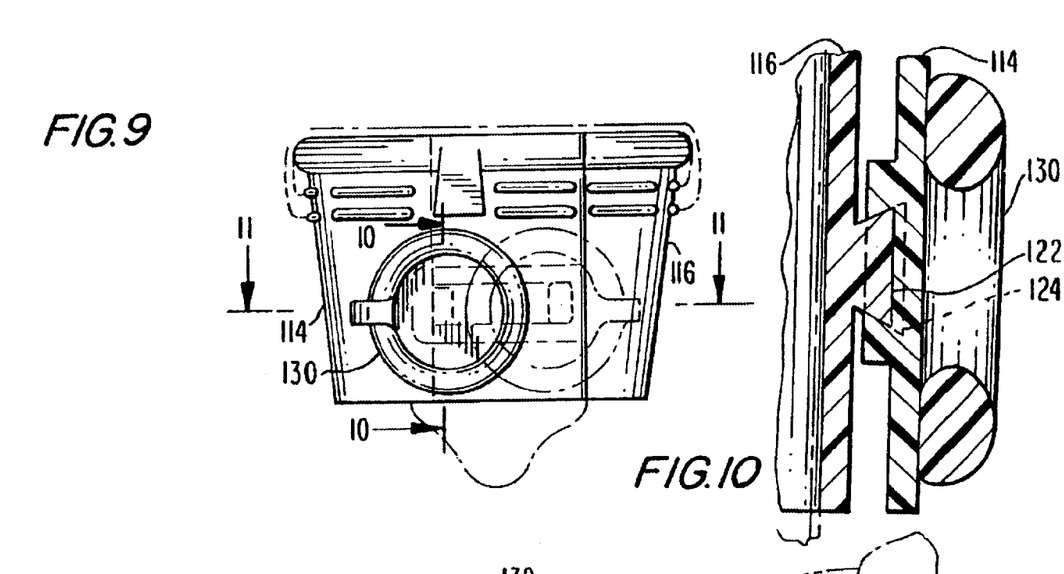
FIG. 9 is a side elevational view of a condom applicator in accordance with a third preferred embodiment of the present invention, in its compressed configuration and with an attached condom shown in phantom.
FIG. 10 is a cross-sectional view of the condom applicator of FIG. 9 taken along the direction of the arrows.
Figure 11:
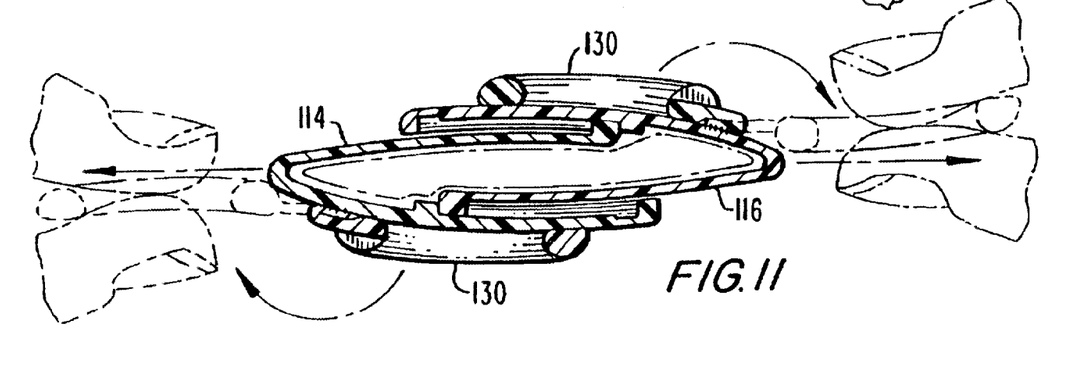
FIG. 11 is a top view of the condom applicator of FIG. 9 in the process of being opened to its expanded configuration.

Alternatively, in another embodiment pull tabs or rings 130 can be molded or otherwise attached to one or both halves 114, 116, as shown in FIGS. 9 and 10. As shown in FIG. 11, the pull rings 130 normally lie flat against the outer surface of the applicator. To open the applicator, the pull rings 130 are flipped out as shown by the curved arrows, and then the two halves 114, 116 are pulled apart in the direction of the straight arrow in FIG. 11. The applicator is then fully opened to present the expanded opening 120 by pushing on opposing sides, as shown in FIG. 8.

Figure 12:
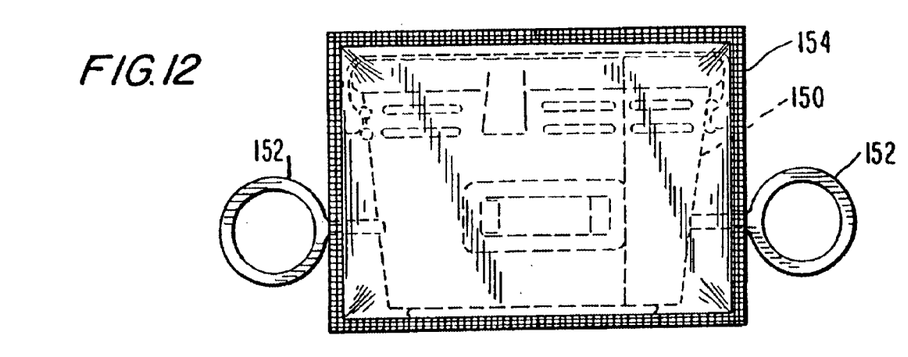
FIG. 12 is a side elevational view of a condom applicator in accordance with a fourth preferred embodiment of the present invention in its compressed configuration.
Figure 13:
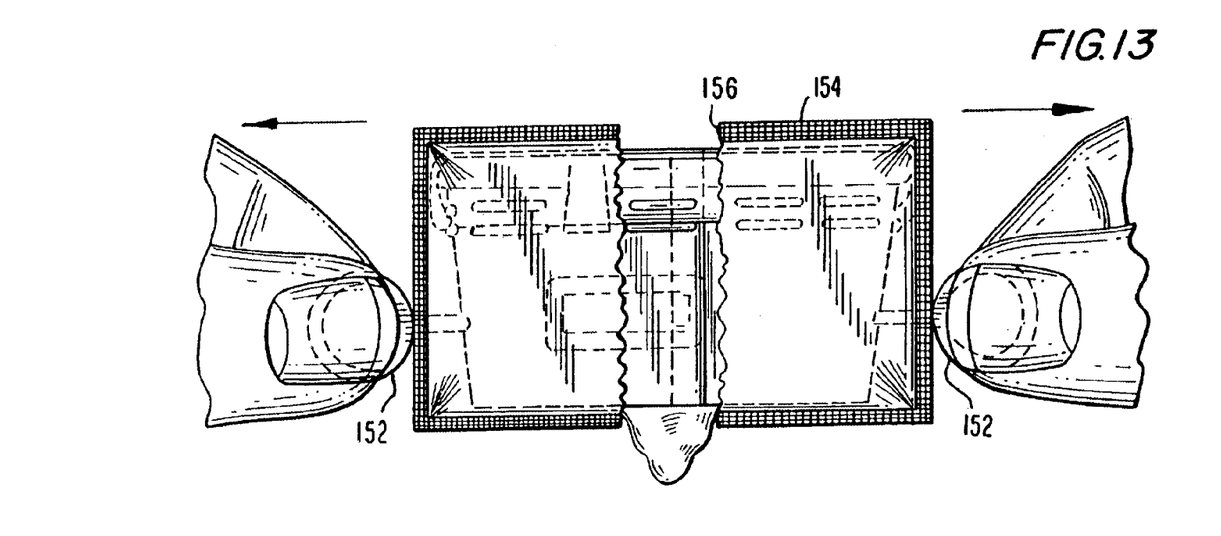
FIG. 13 is a side view of the condom applicator of FIG. 12 in the process of being opened to its expanded configuration.

As a further alternative, pull tabs or rings 152 can be molded or otherwise attached to the external packaging 154 of a condom/applicator device 150, as shown in FIG. 12, with the external packaging 154 being connected in turn to the ends or edges of the applicator 150 so as to transfer the pulling force directly to the applicator halves in order to extend them to their fully open position, as shown in FIG. 13. This pulling force may also be used to open the external packaging 154 by tearing a perforation 156.

At the stage when the halves 114, 116 are pulled apart and locked but the opening of the upper open end 104 is still flat, the bead 32 of the condom 1 has been stretched somewhat, but not enough to permit application of the condom 1. Moving the applicator 100 to its fully expanded configuration with the expanded opening sized to permit axial insertion of the penis, the user manually applies compressive pressure on the halves 114, 116 to cause them to bow so that the opening forms the approximately circular or substantially elliptical expanded opening cross-section. The condom bead 32, surrounding the expanded opening 120, is therefore likewise expanded to the appropriate size for application.

Because of the stops 126, the halves 114, 116 do not slide back together under the manual compressive pressure or under the compressive pressure of the stretched condom bead 32.

The user may now center the penis over the flat cross-section of the condom 1 and begin the application procedure by which the bead 32 may be manually rolled out of the notch between the rows of ridges 118 over the ridges and off of the applicator 100 directly onto the penis, with the subsequent removal of the applicator 100. To ease application further, prior to removing the bead 32 from the rows of ridges 118, the penis may be inserted into and possibly through the applicator 100, thus pulling the flat cross-section over the penis and partially unrolling the condom 1 on the penis, and thus holding the applicator 100 on the penis when the penis is inserted into or through the applicator 100 as far as desired or possible, depending on the particular user.

Figure 14:
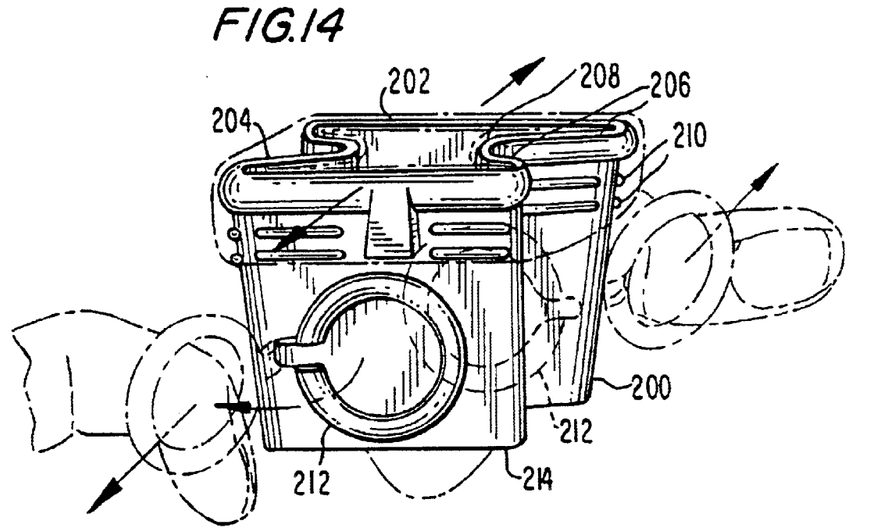
FIG. 14 is a perspective view of a condom applicator in accordance with a fifth preferred embodiment of the present invention, with an attached condom shown in phantom, in the process of being opened from its compressed configuration to its expanded configuration.

FIG. 14 illustrates another preferred embodiment of the applicator in accordance with the present invention. In this embodiment, the applicator 200 (with the condom 1 shown in phantom) is not made of separate halves, but rather is formed of a single piece made of a material such as plastic. The wall 202 is divided into six regions or wall portions, of which two opposing wall portions 204, 206 are molded or formed to be thicker than the remainder of the wall 202, allowing the two wall portions 204, 206 to be formed to resemble pleats 208 in a bellows (or in other words a "living hinge"), thus permitting radial expansion of the applicator 200.

Like the embodiment of FIG. 6, the applicator 200 may have two rows of ridges 210 to hold a condom bead in place in the space therebetween.

Similarly, the applicator may include opposed pull tabs 212 to assist in expanding the applicator 200 to stretch the opening of an attached condom. In this embodiment, however, because of the six sides, the applicator 200 may naturally expand a small amount, leaving the lower opening 214 large enough for the insertion of fingertips in order to pull the applicator 200 open.

FIG. 14 illustrates the applicator 200 (without the pull tabs) at an intermediate stage between its compressed configuration, in which the wall portions all lie flat on top of each other, and its expanded configuration, in which the wall portions are pulled apart to form a six-sided figure with an upper opening that is as rounded as possible. Resistance to the compressive force used to expand the applicator 200 and the compressive force exerted by the stretched condom could be achieved either by a set of protrusions riding in tracks, as in the embodiment of FIG. 6, or by an external holder which may or may not be a part of the applicator 200 and which would serve to hold the thicker wall portions 204, 206 in their extended, expanded state.

Figure 15:
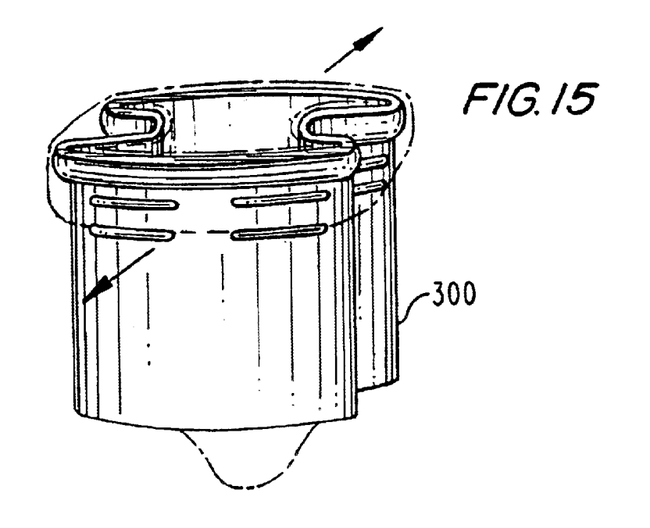
FIG. 15 is a perspective view of a condom applicator in accordance with a sixth preferred embodiment of the present invention, with an attached condom shown in phantom, in the process of being opened from its compressed configuration to its expanded configuration.

FIG. 15 illustrates yet another preferred embodiment, which takes advantage of the natural elasticity of polymers and/or of "spring metals" like aluminum and stainless steel. In this embodiment, a section of the proposed elastic material, shaped similarly to the wall 202 of the embodiment of FIG. 14, is formed so that when compressed prior to packaging at the factory ut achieves a serpentine folded and substantially flattened compressed configuration. The applicator 300 is held in this compressed configuration by a band or other restraining means while in its packaging. When released from its package and from the restraining means holding it in its compressed configuration, the action of the applicator 300 in expanding back to its normal approximately circular or elliptical cross-sectional shape transfers sufficient force to the condom to expand it to its maximum cross-sectional size.

Figure 16:
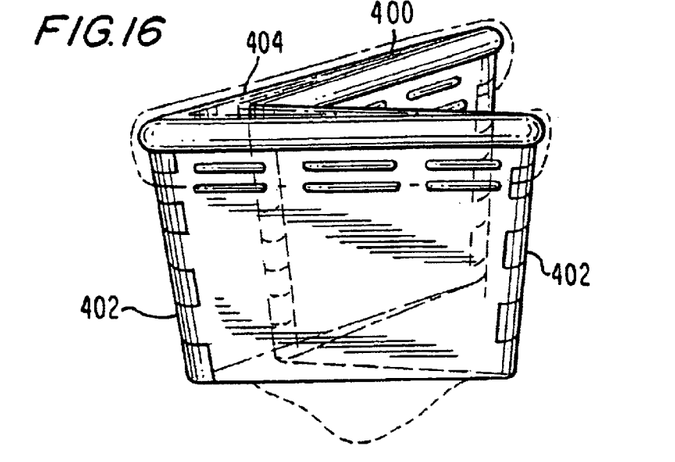
FIG. 16 is a perspective view of a condom applicator in accordance with a seventh preferred embodiment of the present invention, in its compressed configuration and with an attached condom shown in phantom.
Figures 17, 18:
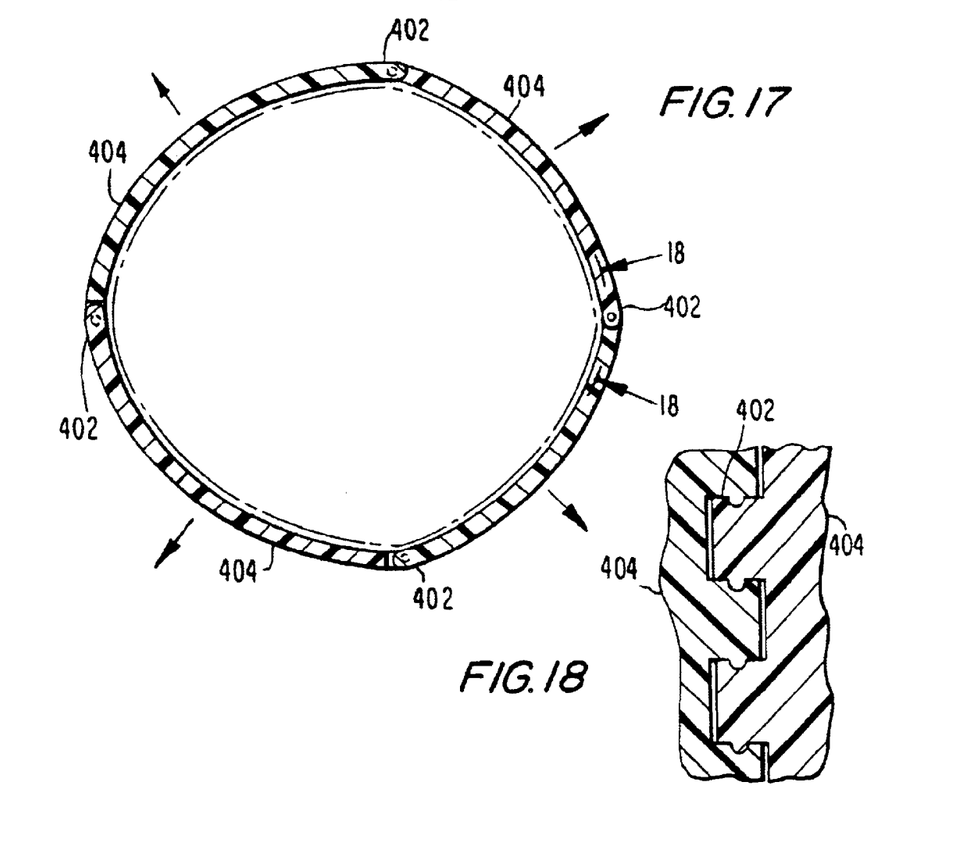
FIG. 17 is a top view of the condom applicator of FIG. 16 after having been opened to its expanded configuration.
FIG. 18 is a cross-sectional view of the condom applicator of FIG. 17 taken along the direction of the arrows 18.

A further embodiment of an applicator 400 illustrated in FIGS. 16–18 uses hinges 402, rather than pleats as in FIG. 14, to expand the applicator 400. Here only four wall portions 404 are used. The hinges 402 have an internal locking mechanism to lock them when the sections 404 of the applicator 400 held by the hinges 402 are fully unfolded.

Figure 19:
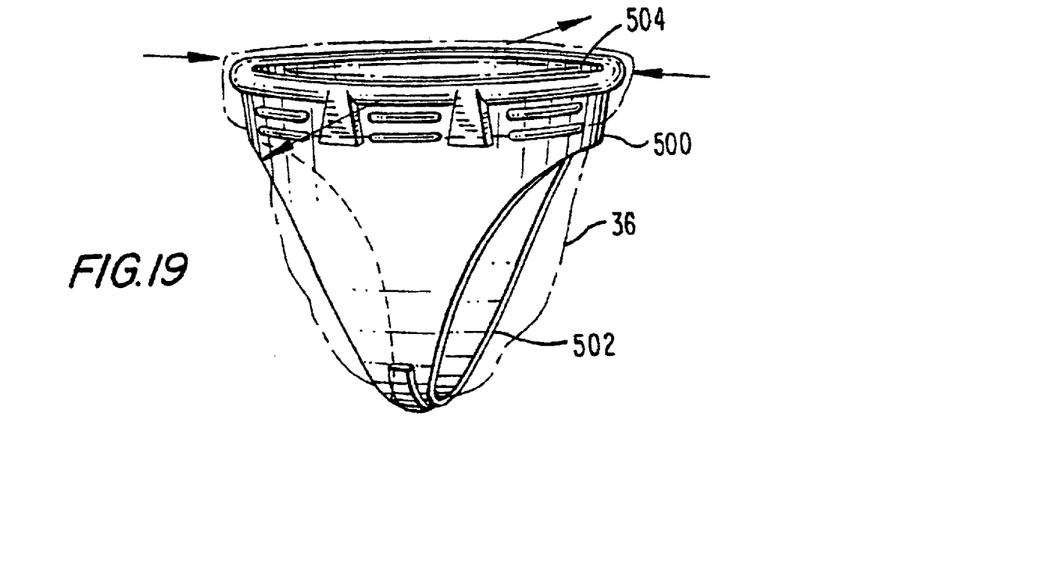
FIG. 19 is a perspective view of a condom applicator in accordance with an eighth preferred embodiment of the present invention, in its compressed configuration and with an attached condom shown in phantom.

Another embodiment, shown in FIG. 19, initially stretches the condom placed on it, as do the applicators of Kassman and Wood. However, unlike those prior applicators, the applicator 500 here has a partially open lower end 502 opposite the upper opening 504 on which the condom is placed. This lower end 502 facilitates the placement of the condom on the penis by allowing the penis to be inserted into the applicator 500.

Figure 20:
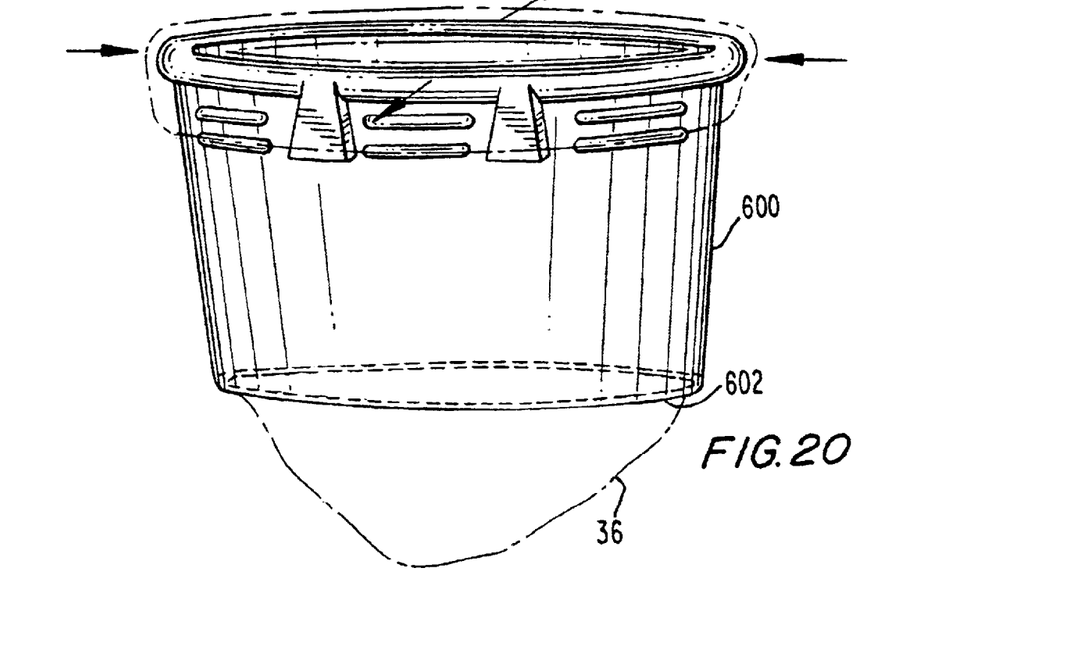
FIG. 20 is a perspective view of the condom applicator of FIG. 19 after having been opened to its expanded configuration.
Figure 21:
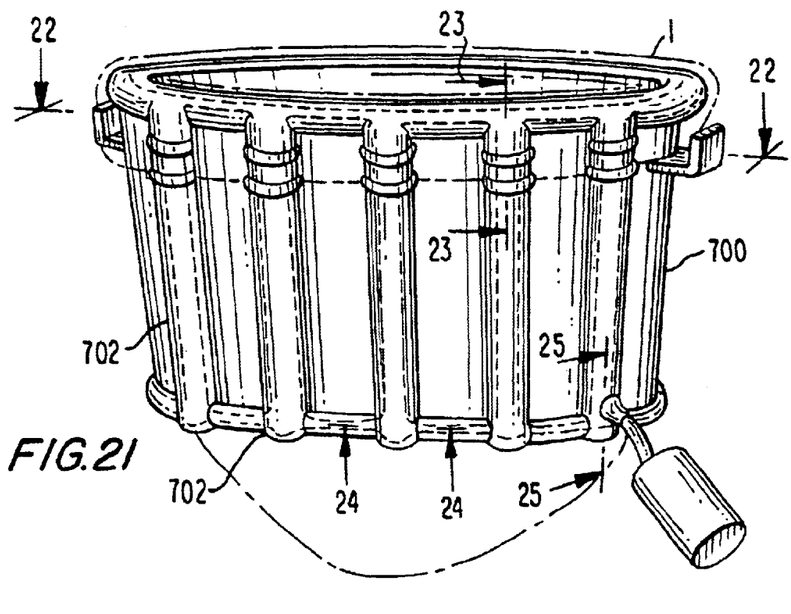
FIG. 21 is a perspective view of a condom applicator in accordance with a ninth preferred embodiment of the present invention, in its compressed configuration and with an attached condom shown in phantom.
Figure 22:
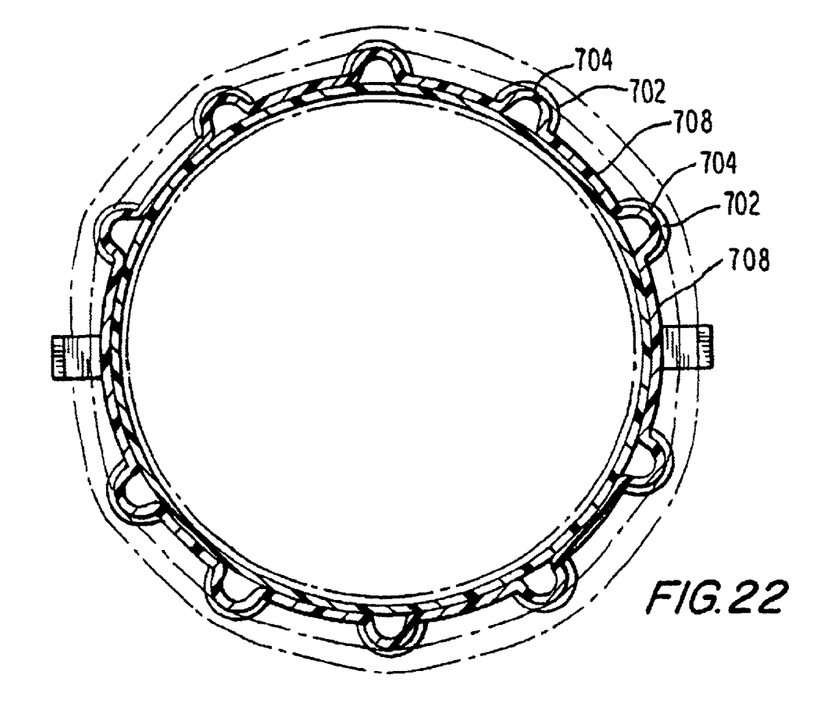
FIG. 22 is a cross-sectional view of the condom applicator of FIG. 21 after having been opened to its expanded configuration taken along arrows 22.

In a variation shown in FIG. 20, the applicator 600 has a completely open lower end 602, enabling the penis to be inserted completely through the applicator 600 into the tip 36 of the condom, if desired.

Figures 23, 24, 25:
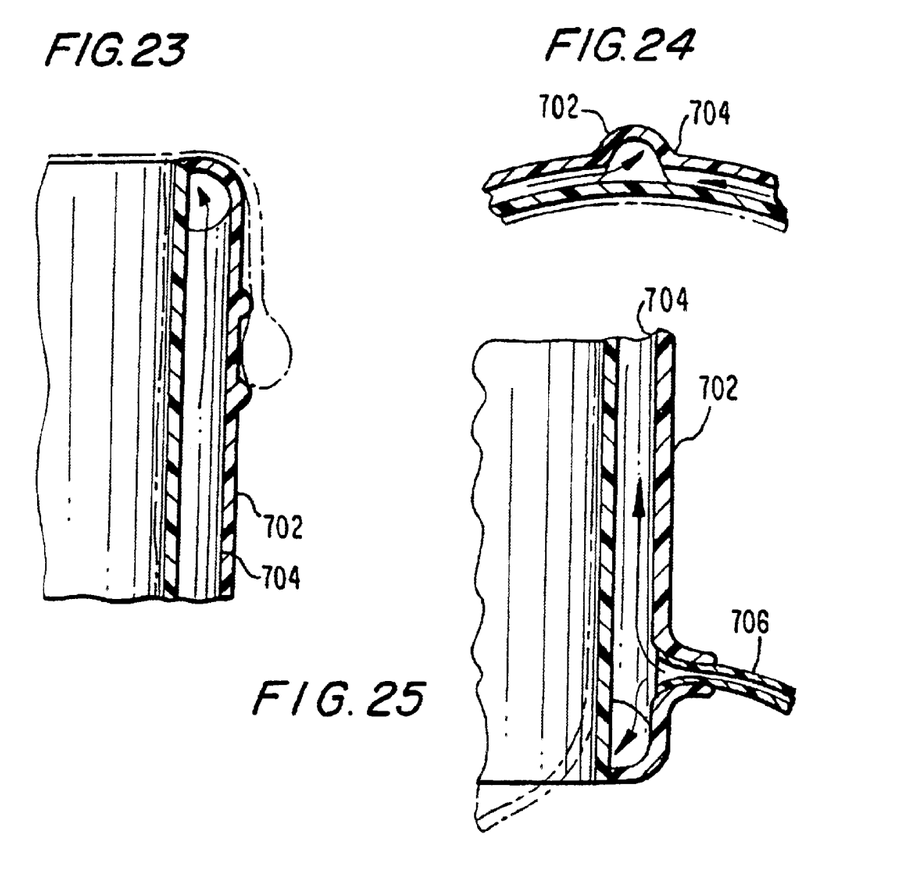
FIG. 23 is a cross-sectional view of the condom applicator of FIG. 21 taken along arrows 23.
FIG. 24 is a cross-sectional view of the condom applicator of FIG. 21 taken along arrows 24.
FIG. 25 is a cross-sectional view of the condom applicator of FIG. 21 taken along arrows 25.

In another embodiment illustrated in FIGS. 21–25, the applicator 700 has pleated sections 702 around its entire circumference. Microtubules 704 are found in each pleated section 702. As packaged, the condom 1 is mounted unstretched on the applicator 700. When it is desired to place the condom on the penis, air or some other expansive substance is introduced into the microtubules 704 in the direction of the arrows in FIGS. 24 and 25 by a source of such expansive substance internal or external to the applicator 700, for example through a tube 706 as shown in FIG. 25. The introduction of the expansive substance expands the applicator 700 by pulling apart the pleated sections 702 along their respective pleats 708, and the condom also expands with the applicator 700 on which it is mounted. In such an expanded state, the condom can be easily applied to the penis.

Figure 26:
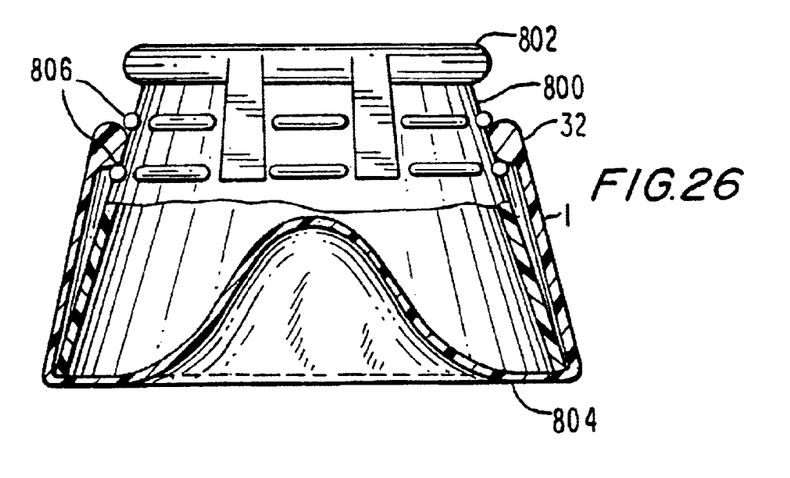
FIG. 26 is a side view, partly cut away, of a condom applicator in combination with a condom in accordance with a tenth embodiment of the present invention.

A further embodiment is shown in FIG. 26 and differs from the previous embodiments in that the applicator 800 only partially stretches the condom 1 mounted on it. The rolled up portion or bead 32 is unstretched, the upper open end 802 of the applicator 800 being of sufficiently small diameter so that this portion of the condom is unstretched. The remainder of the condom is stretched over the larger diameter lower open end 804 of the applicator 800. The condom is applied by placing the lower open end 804 in front of the penis, removing the condom bead from its mount 806 and moving it back onto the penis. For ease of application, the penis can be placed into the applicator 800 so that the applicator is held on the penis while the condom is applied.

It is further noted that in the embodiment of FIG. 26, if the condom 1 is mistakenly attached over the upper open end 802 at the factory, it can still be applied in substantially the same manner described above.

While the disclosed applicators and methods for using them have been particularly shown and described with respect to the preferred embodiments, it is understood by those skilled in the art that various modifications in form and detail may be made therein without departing from the scope and spirit of the invention. Accordingly, modifications such as those suggested above, but not limited thereto are to be considered within the scope of the invention, which is to be determined by reference to the appended claims.

I claim:

1. A condom applicator for supporting a condom, the condom in a substantially unstretched condition having an inner diameter defining a condom circumference at an open cross-section thereof, said applicator comprising:

an axial tubular wall having first and second axially opposed open ends and an outer surface, said wall having a compressed configuration in which said first open end defines a compressed opening having an applicator circumference not substantially greater than the condom circumference, said wall further having an expanded configuration in which said first open end defines an expanded opening greater than said applicator circumference and sized to permit axial insertion of a penis; and means for detachably securing the condom at said first open end such that the condom circumference conforms to applicator circumference at the outer surface of said wall with the cross-section of the condom covering said first open end, whereby the cross-section of the condom is expanded to the size of said expanded opening by expanding said wall from its compressed configuration with the condom secured thereto to its expanded configuration with the condom secured thereto.

2. The applicator of claim 1, wherein said expanded opening is substantially elliptical.

3. The applicator of claim 1, wherein said wall includes at least two axially extending wall portions, said wall portions being connected to slide without disconnection between said compressed configuration with said wall panels lying substantially flat in overlapping relation and said expanded configuration with said wall panels meeting substantially axial edge to axial edge.

4. The applicator of claim 3, wherein said wall includes at least four axially extending wall portions, each wall portion joined at its left and right axial edges to a respective adjacent wall portion by a respective axial fold line, said wall being foldable along said axial fold lines into said compressed configuration.

5. The applicator of claim 4, wherein each axial fold line includes a hinge.

6. The applicator of claim 4, wherein said wall includes six axially extending wall portions.

7. The applicator of claim 1, where an upper portion of the condom forms a circular bead, and wherein said securing means includes at least one ridge projecting outwardly from said outer surface of said wall and extending substantially parallel to said first open end at least partially around said wall, the bead of the condom being fittable against said ridge to be restrained from slipping toward said first open end by said ridge.

8. The applicator of claim 7, wherein said securing means includes two axially spaced ridges projecting outwardly from said outer surface of said wall and extending substantially parallel to said first open end at least partially around said wall, the bead of the condom being positionable between said two ridges to be restrained thereby from slipping toward either open end.

9. The applicator of claim 1, where an upper portion of the condom forms a circular bead, and wherein said securing means includes at least one notch extending at least partially through said wall, the bead of the condom being fittable at least partially within said notch to be restrained from slipping toward said first open end by said notch.

10. The applicator of claim 9, wherein said notch is a window extending entirely through said wall.

11. The applicator of claim 9, wherein said securing means includes a plurality of said notches extending at least partially through said wall and extending along a circle substantially parallel to said first open end.

12. The applicator of claim 11, wherein each of said notches is a window extending entirely through said wall.

13. The applicator of claim 1, further comprising:

means for assisting expansion of said wall from its compressed configuration with the condom secured thereto to its expanded configuration with the condom secured thereto, wherein said expansion assistance means includes a pull tab.

14. The applicator of claim 13, wherein said wall in its compressed configuration is folded to have an interior fold line at which the outer surface of two portions of said wall are in contact, and wherein said pull tab is attached substantially at said interior fold line.

15. The applicator of claim 14, wherein said pull tab extends beyond said applicator circumference.

16. The applicator of claim 14, wherein said expansion assistance means further includes at least one gripping section on said outer surface of said wall at a position opposed to said pull tab, said gripping section having a frictional surface suitable for engaging skin, whereby said applicator may be held by hand at said gripping section while said wall is expanded from its compressed configuration to its expanded configuration by tension of said pull tab.

17. The applicator of claim 1, further comprising:

means for assisting expansion of said wall from its compressed configuration with the condom secured thereto to its expanded configuration with the condom secured thereto, wherein said expansion assistance means includes at least one gripping section on said outer surface of said wall, said gripping section having a frictional surface suitable for engaging skin, whereby said applicator may be held by hand at said gripping section while said wall is expanded from its compressed configuration to its expanded configuration.

18. The applicator of claim 1, wherein all existing edges and interior projections of said applicator are rounded to avoid skin abrasion.

19. The applicator of claim 1, further comprising a layer of silicone lubricant.

20. A condom application device comprising:
a condom, said condom in a substantially unstretched condition having an inner diameter defining a condom circumference at an open cross-section thereof; and
a condom applicator for supporting said condom, said applicator comprising:
an axial tubular wall having first and second axially opposed open ends and an outer surface,
said wall having a compressed configuration in which said first open end defines a compressed opening having an applicator circumference not substantially greater than said condom circumference,
said wail further having an expanded configuration in which said first open end defines an expanded opening greater than said applicator circumference and sized to permit axial insertion of a penis, and
means for detachably securing said condom at said first open end such that the condom circumference conforms to the applicator circumference at the outer surface of said wall with said cross-section of said condom covering said first open end, whereby said cross-section of said condom is expanded to the size of said expanded opening by expanding said wall from its compressed configuration with said condom secured thereto to its expanded configuration with said condom secured thereto.

21. The device of claim 20, wherein said expanded opening is substantially elliptical.

22. The device of claim 20, wherein an upper portion of said condom forms a circular bead and a lower portion of said condom is unrolled, and wherein said bead is secured to said securing means at said outer surface of said wall and said lower portion of said condom is nested within said wall.

23. The device of claim 20, further comprising:
means for assisting expansion of said wall from its compressed configuration with said condom secured thereto to its expanded configuration with said condom secured thereto, wherein said expansion assistance means includes at least one gripping section on said outer surface of said wall, said gripping section having a frictional surface suitable for engaging skin, whereby said applicator may be held by hand at said gripping section while being expanded from its compressed configuration to its expanded configuration.

24. The device of claim 23, wherein said wall in its compressed configuration is folded to have an interior fold line at which the outer surface of two portions of said wall are in contact, and wherein said expansion assistance means further includes a pull tab attached substantially at said interior fold line at a position opposed to said at least one gripping section and extending beyond said applicator circumference, whereby said applicator may be held by hand at said gripping section while being expanded from its compressed configuration to its expanded configuration by tension on said pull tab.

25. A method of packaging a device including a condom and a condom applicator supporting the condom, said method comprising the steps of:
preparing a condom to have, in a substantially unstretched condition thereof, an inner diameter defining a condom circumference at an open cross-section thereof;
preparing a condom applicator, the applicator having an axial tubular wall having first and second axially opposed open ends and an outer surface, the wall having a compressed configuration in which the first open end defines a compressed opening having an applicator circumference not substantially greater than the condom circumference, the wall further having an expanded configuration in which the first open end defines an expanded opening greater than the applicator circumference and sized to permit axial insertion of a penis;
placing the applicator in its compressed configuration;
detachably securing the condom to the applicator in its compressed configuration at the first open end such that the condom circumference conforms to the applicator circumference at the outer surface of the wall with the cross-section of the condom covering the first open end; and
packaging the applicator to maintain the applicator in its compressed configuration until use.

26. The method of claim 25, wherein said packaging step includes the step of applying a keeper band to the applicator in its compressed configuration to maintain the applicator in it compressed configuration.

27. A method of using a packaged device including a condom and a condom applicator supporting the condom, wherein the packaged device was prepared by a method comprising the steps of:
preparing a condom to have, in a substantially unstretched condition thereof, an inner diameter defining a condom circumference at an open cross-section thereof;
preparing a condom applicator, the applicator having an axial tubular wall having first and second axially opposed open ends and an outer surface, the wall having a compressed configuration in which the first open end defines a compressed opening having an applicator circumference not substantially greater than the condom circumference, the wall further having an expanded configuration in which the first open end defines on expanded opening greater than the applicator circumference and sized to permit axial insertion of a penis;
placing the applicator in its compressed configuration;
detachably securing the condom to the applicator in its compressed configuration at the first open end such that the condom circumference conforms to the applicator circumference at the outer surface of the wall with the cross-section of the condom covering the first open end; and
packaging the applicator to maintain the applicator in its compressed configuration until use,
said method of using the packaged device comprising the steps of;
removing the device from any packaging maintaining the applicator in its compressed configuration; and
expanding the applicator from its compressed configuration with the condom secured thereto to its expanded configuration with the condom secured thereto, whereby the cross-section of the condom is expanded to the size of the expanded opening.

28. A method of using a packaged device including a condom and a condom applicator supporting the condom, wherein the condom has, in a substantially unstretched condition thereof, an inner diameter defining a condom circumference at an open cross-section thereof, and the applicator has an axial tubular wall having first and second axially opposed open ends and an outer surface, the wall having a compressed configuration in which the first open end defines a compressed opening having an applicator circumference not substantially greater than the condom circumference, the wall further having an expanded configuration in which the first open end defines an expanded opening greater than the applicator circumference and sized to permit axial insertion of a penis, the condom being detachably secured to the applicator in its compressed configuration at the first open end such that the condom circumference conforms to the applicator circumference at the outer surface of the wall with the cross-section of the condom covering the first open end and the applicator being packaged to maintain the applicator in its compressed configuration until use,     said method of using the packaged device comprising the steps of:

removing the device from any packaging maintaining the applicator in its compressed configuration; and     expanding the applicator from its compressed configuration with the condom secured thereto to its expanded configuration with the condom secured thereto, whereby the cross-section of the condom is expanded to the size of the expanded opening.

29. A method of packaging a device including a condom and a condom applicator supporting the condom, said method comprising the steps of:

preparing a condom to have, in a stretched condition thereof, an inner diameter defining a condom circumference at an open cross-section thereof;

preparing a condom applicator, the applicator having an axial tubular wall having first and second axially opposed ends and an outer surface, the first end being open and the second end being at least partially open, the wall having a compressed configuration in which the first open end defines a compressed opening having an applicator circumference not substantially greater than the condom circumference, the wall further having an expanded configuration in which the first open end defines an expanded opening greater than the applicator circumference and sized to permit axial insertion of a penis;

detachably securing the condom to the applicator at the first open end when the applicator wall is in the compressed configuration such that the condom circumference conforms to the applicator circumference at the outer surface of the wall with the cross-section of the condom covering the first open end; and packaging the applicator to maintain the applicator in the compressed configuration with the condom secured thereto until use.

\* \* \* \* \*